United States Patent
Parkhideh

(10) Patent No.: US 7,803,366 B2
(45) Date of Patent: *Sep. 28, 2010

(54) METHODS AND COMPOSITIONS THAT ENHANCE BIOAVAILABILITY OF COENZYME-Q10

(75) Inventor: Daryoush Parkhideh, Old Field, NY (US)

(73) Assignee: NBTY, Inc., Ronkonkoma, NY (US)

(*) Notice: Subject to any disclaimer, the term of this patent is extended or adjusted under 35 U.S.C. 154(b) by 149 days.

This patent is subject to a terminal disclaimer.

(21) Appl. No.: 12/197,686

(22) Filed: Aug. 25, 2008

(65) Prior Publication Data

US 2009/0054530 A1 Feb. 26, 2009

Related U.S. Application Data

(62) Division of application No. 10/840,423, filed on May 7, 2004, now Pat. No. 7,438,903.

(51) Int. Cl.
*A61K 38/43* (2006.01)
*A61K 47/00* (2006.01)

(52) U.S. Cl. ............. 424/94.1; 424/439; 977/501; 977/775

(58) Field of Classification Search ............... None
See application file for complete search history.

(56) References Cited

U.S. PATENT DOCUMENTS

| 3,536,809 | A | 10/1970 | Applezweig |
|---|---|---|---|
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,221,778 | A | 9/1980 | Raghunathan |
| 4,483,873 | A | 11/1984 | Ohashi et al. |
| 5,059,595 | A | 10/1991 | Le Grazie |
| 5,073,543 | A | 12/1991 | Marshall et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,566 | A | 3/1998 | Lewis |
| 5,989,583 | A | 11/1999 | Amselem |
| 6,045,826 | A | 4/2000 | Borowy-Borowski et al. |
| 6,056,971 | A | 5/2000 | Goldman |
| 6,197,349 | B1 | 3/2001 | Westesen et al. |
| 6,300,377 | B1 | 10/2001 | Chopra |
| 6,441,050 | B1 | 8/2002 | Chopra |
| 5,120,548 | A1 | 11/2008 | McClelland et al. |
| 2009/0181076 | A1* | 7/2009 | Prestidge et al. ............ 424/450 |

FOREIGN PATENT DOCUMENTS

| WO | 94/20072 | A1 | 9/1994 |
|---|---|---|---|
| WO | 95/05164 | A1 | 2/1995 |
| WO | 99/39700 | A1 | 8/1999 |
| WO | 02076441 | A1 | 10/2002 |

OTHER PUBLICATIONS

Ebert, Pharm. Tech, 1(5):44-50(1977).
Leninger et al. p. 243, Fig 9-2 and "Triacylglycerols and Fatty Acids Esters of Glycerol" Principles of Biochemistry Worth Publ., New York (1993).

* cited by examiner

*Primary Examiner*—Herbert J. Lilling
(74) *Attorney, Agent, or Firm*—Hoffmann & Baron, LLP

(57) ABSTRACT

Bioavailability of Coenzyme-Q 10 ("Co-Q10"), an oil-soluble substance, can be enhanced in a subject by modifying, e.g. nanonizing or charging, the form of Co-Q10. Co-Q10 bioavailability also can be enhanced by administering Co-Q10 to the subject as an oil (lipid)-based and water (hydro)-based mixed composition, along with other optional components, such as oils, resins and other carriers. Accordingly, the invention provides various Co-Q10 compositions, e.g. compositions comprised of (i) Co-Q10 dissolved in one or more Co-Q10-soluble oils and (ii) Co-Q10 in admixture with at least one water-dispersible agent. A Co-Q10 complex of the invention, therefore, yields an increased cell absorption rate, as well as an enhanced percentage of Co-Q10 peak absorption, compared to previously known compounds. Methods for making and using the aforementioned compositions also are provided.

20 Claims, No Drawings

METHODS AND COMPOSITIONS THAT ENHANCE BIOAVAILABILITY OF COENZYME-Q10

CROSS-REFERENCE TO RELATED APPLICATION

This application is a divisional application of co-pending U.S. application Ser. No. 10/840,423, filed on May 7, 2004.

BACKGROUND OF THE INVENTION

Coenzyme Q10 ("Co-Q10"), a valuable nutrient to the body, is a naturally occurring coenzyme having the chemical nomenclature 2,3-dimethoxy-5-methyl-6-decaprenyl-1,4-benzoquinone. Co-Q10—also known by the names ubiquinone, ubidecarenone and Vitamin Q—is classified as a fat soluble quinone and is produced by the human body naturally in very small quantities.

Co-Q10 levels in plasma generally decrease with age and season. And certain individuals experience prematurely decreasing Co-Q10 levels or suffer from a disorder or condition that hinders Co-Q10 production.

Co-Q10 has been identified as playing various roles in supporting homeostasis. It is well known, for example, that Co-Q10 is an antioxidant with the potential to protect against age-related degeneration and as an adjuvant vitamin to prevent or treat many diseases. To this end, U.S. Pat. No. 5,989,583 notes Co-Q10's promise in the treatment of periodontal disease, certain blood circulation diseases, impaired memory, fatigue, coronary disease, irregular heartbeat, high blood pressure, immune system impairment, and the aging process. Further, Co-Q10 is believed to have significant health benefits for congestive heart failure. Moreover, coenzyme Q10 has been reported to enhance oxygen uptake and processing in cells.

Generally, individuals that wish to boost natural Coenzyme-Q10 levels do so by ingesting Co-Q10 in the form of food supplements, such as capsule, tablet, liquid or softgel forms. Softgels are regarded generally as the most popular Co-Q10 delivery method.

Due to its isoprenoid side chain, however, Co-Q10 is extremely lipophilic. When administered in the form of an oil solution or some kind of water and/or oil suspension or emulsion, lipophilic compounds usually show a poor bioavailability, meaning a low concentration and a long build-up time of the compound in the systemic circulation. This lack of bioavailability usually is independent of the administration route (topical, oral, or parenteral). There has been, therefore, a desire to find ways of overcoming this inherent drawback to Co-Q10.

Various attempts of increasing Co-Q10 bioavailability through the use of solubility-enhancing agents have been reported. For instance, U.S. Pat. No. 4,483,873 discloses aqueous solutions of Co-Q10 that contain hydrogenated lecithin in an attempt to increase Co-Q10 bioavailability. U.S. Pat. No. 6,045,826 discloses water-soluble compositions containing a lipophilic compound, e.g. Co-Q10, and a single solubilizing agent having both hydrophobic and hydrophilic moieties. U.S. Pat. Nos. 6,056,971 and 6,441,050 disclose methods for solubilizing water-insoluble dietary supplements in liquid form, such as Co-Q10 in a softgel, by mixing Co-Q10 with, among other things, an edible polyhydric alcohol solvent. U.S. Pat. No. 6,300,377 teaches the formulation of a Co-Q10 composition that omits polyhydric alcohol, but includes other agents to help improve solubility, including a glyceryl ester molecule having one to three $C_2$ to $C_7$ acyl groups.

Despite the foregoing attempts to increase Co-Q10 solubility, relatively low solubility levels continue to plague affective Co-Q10 assimilation by the body. As an example, Co-Q10 dosage forms to date, e.g. softgel capsules, must remain relatively large in size, having an approximate formula weight of 1000 mg. This translates into a softgel that is approximately 1" long, which can be difficult to swallow—especially for the elderly, who stand to benefit the most from Coenzyme-Q 10 supplements.

There is, therefore, a continuing need to improve Co-Q10 bioavailability beyond the level realized today. The present invention satisfies this and other needs.

SUMMARY OF THE INVENTION

Accordingly, it is an object of the invention to provide Co-Q10 formulations and compositions having enhanced bioavailability.

It is a further object of the invention to provide such formulations and compositions which do not require a solvent such as a polyhydric alcohol.

It is still a further object of the invention to provide methods of making and using Co-Q10 formulations and compositions having enhanced bioavailability.

These and other objects of the invention are elaborated upon below.

The invention provides modified Co-Q10 formulations, as well as novel Co-Q10 compositions having a mixture of various bioavailability-enhancing components. Modified Co-Q10 formulations include nanoparticulate and charged (e.g., ionically charged) Co-Q10. Mixed Co-Q10 compositions of the invention can include one or more bioavailability-enhancing components, which include one or more hydro-based components and one or more lipid-based components. A mixed Co-Q10 composition contains. Co-Q10 in a conventionally available format, nanosized Co-Q10 and/or charged Co-Q10, as contemplated herein.

Thus, in one embodiment, the invention relates to a composition, comprising (i) an effective amount of coenzyme-Q10 in nanosized form and (ii) a suitable carrier or excipient therefor. This composition could further comprise at least one lipid-based or lipid-soluble compound and optionally at least one hydro-dispersible or hydro-soluble compound. The lipid-based or lipid-soluble compound makes the coenzyme Q10 lipid-based or lipid-soluble and the hydro-dispersible or hydro-soluble compound makes the coenzyme Q10 hydro-dispersible or hydro-soluble. In one embodiment, the lipid-based or lipid-soluble compound is selected from the group consisting of tocopherols, vegetable oils and lecithins. The tocopherols may include, but are not limited to, an alpha tocopherol, a beta tocopherol, or a gamma tocopherol. The vegetable oils of the invention may include, but are not limited to, palm, coconut, palm kernel, palm stearin, coffee, soya, soybean oil, safflower, canola, rapeseed, flax, cotton, cottonseed, wheat germ oil, maize germ oil, sunflower, lucerne oil, poppy oil, red kuri oil, sesame oil, rapeseed oil, evening primrose oil, millet oil, barley oil, quinoa oil, rye oil, candlenut oil passionflower oil, or rape seed oil. In one embodiment, the hydro-dispersible or hydro-soluble compound is a non-ionic surface active agent, which may be lecithin, polysorbate 80, Olacta, or other similar acting material.

In another embodiment, the above composition contains coenzyme-Q10 that has a net ionic positive or negative charge.

The composition of the invention may be a dietary, nutritional or pharmaceutical composition.

In another embodiment, the invention is directed to a substantially purified formulation of coenzyme-Q10 in nano-sized form or in a form having a net positive or net negative ionic charge.

In another embodiment, the above compositions of the invention comprise a specifically charged resin. For instance, coenzyme-Q10 may be coated on said resin or mixed with inactive resin.

In another embodiment, the invention relates to a method for preparing a composition that comprises coenzyme-Q10 comprising the steps of:

(a) dissolving an amount of coenzyme-Q10 in one or more carriers, such as at least one non-ionic surface active agent, at least one tocopherol and at least one vegetable oil and (b) decreasing the temperature at a rate that prevents or reduces coenzyme-Q10 from eluting out of the mixture.

In another embodiment, the method of the invention relates to coenzyme-Q10 in nanosized form, which is placed in contact with a pre-cooled carrier and maintained at about 30 degrees F. until the coenzyme-Q10 and carrier are combined.

In another embodiment, the invention relates to a method for preparing a composition that comprises coenzyme-Q10 comprising the step of:

(a) combining an amount of coenzyme-Q10 having a net positive or net negative ionic charge with a suitable carrier therefor. The carrier may be a resin.

In another embodiment, the invention relates to a composition comprising (i) an effective amount of coenzyme-Q10 in nanosized form and (ii) a suitable carrier or excipient therefor, wherein said composition does not contain a compound of the following structure

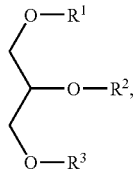

wherein each of R1, R2 and R3 independently is H or a $C_2$ to $C_7$ acyl group.

In another embodiment, the invention relates to a composition consisting essentially of an effective amount of Co-Q10, a rice bran oil extract, a tocopherol, and a non-ionic surface active agent. Each of the fatty acid molecules contained in such rice bran oil extract is a long-chain fatty acid molecule.

In another embodiment, the invention consists essentially of an effective amount of Co-Q10, a rice bran oil extract, a tocopherol, a non-ionic surface active agent and lecithin.

In yet another embodiment, the invention relates to a method for treating a patient suffering from a condition associated with decreased Co-Q10 levels, comprising the steps of administering to said patient an effective amount of the above compositions or formulations of the invention and observing a reduction in severity or frequency of at least one symptom associated with the condition, wherein the condition might be an age-related degenerative disease, periodontal disease, a blood-circulation disease, impaired memory, fatigue, coronary disease, irregular heartbeat, high blood pressure, immune system impairment, or the aging process.

DETAILED DESCRIPTION OF THE INVENTION

The present invention is based on the discovery of various ways to enhance the bioavailability of Coenzyme-Q 10 ("Co-Q10"), an oil-soluble substance, in a subject. As used herein, "enhanced bioavailability" means a fast rate of delivery of Co-Q10 to blood and more importantly to cells where Co-Q10 is beneficial. In some cases, enhanced Co-Q10 bioavailability is the result of modifying the form of Co-Q10, such as by "nanosizing" or "charging" the Co-Q10. In other cases, enhanced Co-Q10 bioavailability can be achieved by combining Co-Q10 with various bioavailability-enhancing components, e.g. a hydrophilic and a hydrophobic component. Further, the invention contemplates products representing the implementation of both of the foregoing advances, namely, one or more compositions that contain modified Co-Q10 and various bioavailability-enhancing components.

The Co-Q10-containing compositions of the invention are made and used in various ways, as further provided herein. Due to their high Co-Q10 bioavailability, compositions contemplated by the invention can be administered to a subject in many ways and used as a dietary or nutritional supplement, or a pharmaceutical agent.

Co-Q10 may be presented to, and absorbed by, the gastrointestinal tract of a subject. The human gastrointestinal tract is a complex system that is capable of absorbing oil (lipid) based and water (hydro) based compounds. A simple example is that water soluble materials such as salt, sugar, and water soluble vitamins are absorbed by the body. Similarly, lipids, and lipid soluble vitamins such as flaxseed oil and vitamin E are also absorbed by human body.

Accordingly, a Co-Q10 formula of the invention that is both lipid-based or lipid-soluble and hydro-dispersible effectively can utilize two distinct channels of absorption in the gastro intestinal tract at the same time. This allows for the formulation of dosage units that contain a smaller proportion of inactive ingredients (solubilizers and carriers) compared to conventionally available dosage units. In the Co-Q10 formula of the invention, the ratio of inactive/active ingredients is lower than known Co-Q10 compositions (for example, lower than Tishcon's product Q-GEL). Enhanced Co-Q10 bioavailability also allows for the formulation of dosage units that contain a lower concentration of Co-Q10 compared to conventionally available dosage units. Thus, a single dosage unit can be prepared, according to the teachings herein, that has a formula weight of about 300 mg, for example, yet have at least the same level of Co-Q10 bioavailability as compared to a conventional 1000 mg formula weight.

Compositions of the invention, therefore, add many benefits over Co-Q10 larger dosage unit compositions used to date. Co-Q10 cell absorption rate is substantially increased, peak absorption percent is substantially higher and cumulative plasma Co-Q10 levels are maintained or enhanced similar to slightly better that prior art.

As used herein, Co-Q10 is defined as a compound represented by the following chemical structure (where n=10):

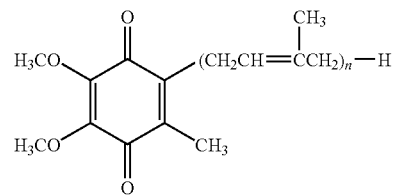

Co-Q10 can be prepared and used in a variety of forms. For those embodiments of the invention that do not call for Co-Q10 in nanosized form, Co-Q10 can be obtained commercially and/or prepared by techniques known in the art in a conventional coarse form. To this end, the particle size of coarse Co-Q10 can be less than about 100μ. Yet, Co-Q10 particles may be reduced in size to less than 100 μm using a conventional milling method, such as airjet or fragmentation milling.

Compositions of the Invention

In one aspect, the invention provides compositions containing a modified form of Co-Q10, such that Co-Q10 bioavailability is increased when administered to a subject. In this regard, a sample of Co-Q10 can be made in nanosized form, which increases bioavailability, inter alia, by increasing the surface area of Co-Q10. In addition or alternative to nanosized Co-Q10 formulations of the invention, Co-Q10 may be modified to carry a net positive or net negative ionic charge. Modified Co-Q10 may be administered to a subject either alone, or in combination with other components.

Nanoparticulate Co-Q10

Thus, the invention provides a substantially purified formulation of coenzyme-Q10 in nanosized form. As used herein, "nanosized" Co-Q10 means Co-Q10 that has an average effective particle size of less than about 1000 nanometers (nm). As used herein, "particle size" refers to a number average particle size as measured by conventional particle size measuring techniques well known to those skilled in the art, such as sedimentation field flow fractionation, photon correlation spectroscopy, disk centrifugation, or other methods known to those of skill in the art. As used herein, an "effective average particle size of less than about 1000 nm" means that at least 80% and preferably at least 90% of the particles have a number average particle size of less than about 1000 nm when measured by the above-noted techniques. In preferred embodiments of the invention, the effective average particle size is less than about 300 nm. With reference to the effective average particle size, it is preferred that at least 95% and, more preferably, at least 99% of the particles have a particle size of less than the effective average, e.g., 1000 nm. In particularly preferred embodiments, essentially all of the particles have a size less than 400 nm, more preferably less than 50 nm.

Co-Q10 can be made nanosized, for example, by dispersing Co-Q10 in a liquid dispersion medium and utilizing, e.g., a dispersion mill in the presence of grinding media to reduce the particle size of the Co-Q10 to an effective average particle size of less than about 1000 nm. If the nanosized formulation contains one or more bioavailability-enhancing components (e.g., a carrier and/or oil), then the particles can be reduced in size in the presence of these components. Alternatively, the particles can be placed in admixture with these other components after attrition.

As indicated, a dispersible mill can be used to reduce the particle size of Co-Q10. Suitable dispersion mills include a ball mill, an attritor mill, a vibratory mill, a planetary mill, media mills, such as a sand mill, and a bead mill. The grinding media for the particle size reduction step can be selected from rigid media, preferably spherical or particulate in form, and having an average size less than about 3 mm and, more preferably, less than about 1 mm. Such media desirably can provide the particles of the invention with shorter processing times and impart less wear to the milling equipment. Suitable grinding media, e.g. those which provide particles having acceptable levels of contamination for the preparation of pharmaceutical compositions, include polymeric grinding media and zirconium oxide, such as 95% ZrO stabilized with magnesia, zirconium silicate, and glass grinding media. Still other media, such as stainless steel, titania, alumina, and 95% ZrO stabilized with yttrium, are contemplated for use in the present invention.

Nanoparticulate Co-Q10 formulations of the invention can be prepared by reducing the size of Co-Q10 at a temperature that is not significantly degrading. Processing temperatures of less than about 80° F.-120° F. generally are preferable. At the same time, the maximum temperature preferably does not reach or exceed the boiling point of Co-Q10. Co-Q 10 is crystalline at room temperature and has a melting point of 49° C. If desired, the processing equipment can be cooled with conventional cooling equipment, with processing being conveniently carried out under conditions of ambient temperature and at processing pressures that are safe and effective for the milling process. For example, ambient processing pressures are typical of ball mills, attritor mills and vibratory mills. Processing pressures up to about 20 psi (1.4 kg/cm.sup.2) are typical of media milling.

Milling preferably is carried out under acidic conditions, e.g., at a pH of from 2-6, preferably 3-5. Acid resistant milling equipment is highly preferred, e.g., equipment fabricated of high grade stainless steel, such as grade 316 SS, or equipment coated with an acid resistant coating.

Other methods of achieving nano-particles are also suitable. They include micro-fluidizer, super critical anti-solvent process, or other means known to the skilled artisan.

Charged Co-Q10

The invention also provides formulations of charged Co-Q10. As used herein, "charged" Co-Q10 refers to a sample of Co-Q10 that carries a net positive or negative charge. A charged Co-Q10 formulation can result in increased bioavailability, based on an enhanced attraction to the intestine.

In this regard, the invention takes advantage of the fact that the intestinal mucosa provides an enormous amount of surface area for the absorption of nutrients and that the mucosal barrier possesses a slight negative charge—a property that either attracts or repels molecules with polar properties. Thus, by altering the ionic properties of the Co-Q10 composition, the invention allows Co-Q10 to have greater intestinal contact which increases bioavailability.

Co-Q10 can be made to have a net positive charge, for example, through the co-administration of an effective amount of a pH-lowering compound to the area where Co-Q10 assimilation is desired. An effective amount of a given Co-Q10 pH-lowering compound is an amount which, when it is released into the intestine, is sufficient to increase the movement of Co-Q10 across the intestinal membrane. The quantity required will vary with several factors, including the type of pH-lowering agent used and the equivalents of protons provided by a given pH-lowering agent. As an example, the required amount is an amount which, when added to a solution of 10 milliliters of 0.1 M sodium bicarbonate, lowers the pH of that sodium bicarbonate solution to no higher than 5.5, and preferably no higher than 4.7, most preferably no higher than 3.0. Enough acid to lower pH, in the foregoing test, to about 2.3 may be used. Preferably, at least about 300 milligrams, and more preferably at least about 400 milligrams of the pH-lowering agent can be used. The foregoing preferences relate to the total combined weight of all pH-lowering agents, where two or more of such agents are used in combination. The oral formulation preferably does not include a concentration of a base that, when released together with the pH-lowering compound, would prevent the pH of the above-described sodium bicarbonate test from dropping to 5.5 or below.

A pH-lowering agent of the invention can be a pharmaceutically acceptable compound that is not toxic in the gastrointestinal tract and is capable of either delivering hydrogen ions (a traditional acid) or inducing higher hydrogen ion content from the local environment. It may also be any combination of such compounds. Preferably, at least one pH-lowering agent for use in the invention has a pKa not higher than 4.2, and preferably not higher than 3.0. It also is preferred that the selected pH-lowering agent has a solubility in water of at least 30 grams per 100 milliliters of water at room temperature.

Examples of compounds that induce higher hydrogen ion content include aluminum chloride and zinc chloride. Pharmaceutically acceptable traditional acids include, but are not limited to acid salts of amino acids (e.g. amino acid hydrochlorides) or derivatives thereof, which include: acid salts of acetylglutamic acid, alanine, arginine, asparagine, aspartic acid, betaine, carnitine, carnosine, citrulline, creatine, glutamic acid, glycine, histidine, hydroxylysine, hydroxyproline, hypotaurine, isoleucine, leucine, lysine, methylhistidine, norleucine, ornithine, phenylalanine, proline, sarcosine, serine, taurine, threonine, tryptophan, tyrosine and valine. Other examples of useful pH-lowering compounds include carboxylic acids, such as acetylsalicylic, acetic, ascorbic, citric, fumaric, glucuronic, glutaric, glyceric, glycocolic, glyoxylic, isocitric, isovaleric, lactic, maleic, oxaloacetic, oxalosuccinic, propionic, pyruvic, succinic, tartaric and valeric acid.

Mixed Co-Q10-Containing Compositions

In another aspect, the present invention is based on the surprising discovery that bioavailability of Co-Q10 can be enhanced in a subject by administering Co-Q10 to the subject, e.g. as a single dosage unit, in the form of an oil (lipid)-based and water (hydro)-based complex. To this end, both the oil- and water-based formats can be absorbed, for instance, by a subject's gastro-intestinal tract. This "dual absorption" enhances the percentage of Co-Q10 that can be absorbed.

Also surprising is that enhanced Co-Q10 bioavailability can be had by administering to a subject a dosage unit that is free of, or at least is substantially free of, water. As used herein, "substantially free of water" means that the amount of water in a given dosage unit does not exceed 20% by weight, and preferably does not exceed 3% by weight of the dosage unit.

Accordingly, the invention provides for compositions and mixtures containing an effective amount of Co-Q10, at least one lipid-based or lipid-soluble compound and one or more hydro-dispersible or hydro-soluble compounds (e.g., water-dispersible agent). Compositions of the invention also may include other components, such as additional oils, resins and other carriers.

The amount of Co-Q10 that is included in a mixed composition of the invention can depend upon the form of Co-Q 10 and may range from about 0.1% to about 90% by weight, preferably about 5% to about 25% by weight, more preferably about 7% to 20% by weight and most preferably about 18% by weight.

A lipid-based or lipid-soluble (lipophilic) compound suitable for use in the present invention includes any one or more of rice bran oil or an extract of rice bran oil, a tocopherol, a combination of CLA, LA, ALA or lecithin. Rice bran oil is absorbed in the small intestine; thus, by at least partially dissolving Co-Q10 therein, Co-Q10 absorption (and bioavailability) can be enhanced. A rice bran oil extracts suitable for use in the present invention can be obtained commercially. Sources include, but are not limited to, Riceland Foods Inc., Arkansas and RITO, Arkansas. The amount of rice bran oil that is included in a mixed composition of the invention ranges from about 0% to about 98% by weight, preferably about 5% to about 60% by weight, more preferably about 10% to about 40% by weight and most preferably about 20% by weight.

A tocopherol suitable for use in the present invention includes any one of Alpha, Beta, Gamma and Delta tocopherols, or any combination thereof. Since tocopherols (including vitamin E) exhibit a relatively high degree of bioavailability, the bioavailability of Coenzyme-Q 10 will be enhanced by being at least partially dissolved in a tocopherol (or a mixture thereof). Co-Q10 then can be absorbed in relatively the same area of the small intestine as where vitamin E is absorbed, for example.

As used herein, a "tocopherol" is represented by the following chemical structure:

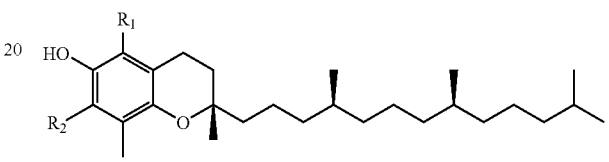

A (R,R,R)-α-Tocopherol is defined where R1=CH3 and R2=CH3; a (R,R,R)-β-Tocopherol is defined where R1=CH3 and R2=H; a (R,R,R)-χ-Tocopherol is defined where R1=H and R2=CH3; and a (R,R,R)-δ-Tocopherol is defined where R1=H and R2=H. Tocopherols suitable for the present invention are commercially available. Sources include but are not limited to Roche, N.J. and ADM-Health, IL.

The amount of tocopherol(s) that is included in a mixed composition of the invention ranges from about 0% to about 98% by weight, preferably about 5% to about 60% by weight, more preferably about 10% to 40% by weight and most preferably about 20% by weight.

A Co-Q10-containing composition of the invention also may include at least one water (hydro)-based complex or surface active agent, which improves the ability of the components of the invention to be solubilized in either the aqueous environment into which they are originally released or into the lipophilic environment of the mucous layer lining the intestinal walls, or both. A water (hydro)-based surface active agent also can be an "uptake enhancer," namely, an agent that facilitates the ease by which Co-Q10 can cross certain portions of the intestinal wall.

Surface active agents can be useful both as solubility enhancers and as uptake/absorption enhancers. For example, detergents and surfactants are useful for solubilizing Co-Q10 into the aqueous environment where they are originally released, as well as enhancing lipophilicity of the components of the invention, especially the peptide active agent, thereby aiding its passage into and through the intestinal mucus.

It is preferred that any surface active agent used as an absorption enhancer be selected from the group consisting of non-ionic surface active agents; anionic surface active agents that are cholesterol derivatives (e.g., bile acids); cationic surface agents (e.g., acyl carnitines and phospholipids); and mixtures of anionic surface active agents with negative charge neutralizers. Negative charge neutralizers include acyl carnitines and cetyl pyridinium chloride. Absorption enhancers preferably are soluble at acidic pH, particularly in the 3.0 to 5.0 range.

A hydro-based complex contemplated herein preferably is, or contains a non-ionic surface active agent. In the context of the Co-Q10-containing compositions of the present invention, non-ionic surface active agents are used to disperse Co-Q10 and any lipid-solubilized portions of the composition. Hydro dispersion will, accordingly, allow more opportunity for Co-Q10 to be absorbed by the body.

As used herein, a "non-ionic surface active agent" is defined as an emulsifying agent suitable for human and/or animal ingestion or absorption. Representative non-ionic surface active agents for use in the present invention include a polysorbate material (e.g., polysorbate 80), Olacta (i.e., oleyl lactylic acid) and lecithin.

As used herein, a "polysorbate material" defines the conventionally available Polysorbate™ or Tween™ products that contain oleate esters of sorbitol and its anhydrides, typically copolymerized with about 20 moles of ethylene oxide per mole of sorbitol and sorbitol anhydride. Polysorbate materials for use in the present invention are water soluble or dispersible in water. In a preferred embodiment, the polysorbate material is a sorbitan mono-9-octadecenoate poly(oxy-1,2-ethanediyl) derivative, which is represented by the following structure, where the sum of w, x, y, and z is 80 ("polysorbate 80"):

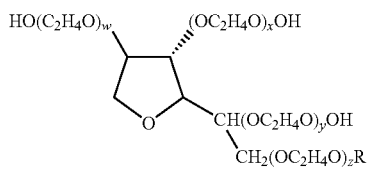

As used herein each of "Olacta" and "oleyl lactylic acid" is a compound based on the interaction between lactic acid and defined as a structure represented by the following chemical structure:

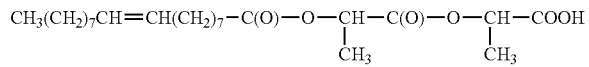

"Oleyl lactylate" is the conjugate base form of oleyl lactylic acid.

The amount of oleyl lactylic acid that is included in a mixed composition of the invention ranges from about 0% to about 98% by weight, preferably about 1% to about 60% by weight, more preferably about 3% to 30% by weight and most preferably about 1% by weight. Oleyl lactylic acid can be obtained commercially. A source includes, but is not limited to American Ingredients Co. (Kansas City, Mo.).

Another optional component of the inventive Co-Q10 compositions is lecithin. Lecithin, which is conventionally used as a liposome-forming agent, is a phospholipid made up of polar heads pointing inward and non-polar tails pointing outward. Liposome formation can be used to uptake of the dual hydrophobic-hydrophilic components of the inventive compositions provided herein. Liposomes such as lecithin can, therefore, improve the "absorbability" of Co-Q10 compositions of the invention in gastrointestinal tract.

If present, the amount of lecithin that is included in a mixed composition of the invention ranges from about 0% to about 98% by weight, preferably about 10% to about 60% by weight, more preferably about 20% to about 50% by weight and most preferably about 30% by weight.

Formulations and compositions of the invention additionally may include a specifically charged resin to further enhance bioavailability. U.S. Pat. No. 4,221,778, which hereby is incorporated-by-reference, discloses ion-exchange resin drug complexes as delivery devices where the resin and drug carry opposite charges. Drug release can be actuated by exchange of the drug with another ion, which dislodges the drug from the resin. Thus, the present invention provides compositions containing ion exchange resins having a Co-Q10 adsorbed thereon to form a Co-Q10-resin complex. Preferably, at least a substantial portion of the Co-Q10-resin complex particles are treated with a solvating agent and provided with a water-permeable diffusion barrier coating. This arrangement provides for a prolonged continuous release of the drug in various in vivo environments, e.g., the gastrointestinal tract.

A wide range of cationic (anionically charged Co-Q10) or anionic (for cationically charged Co-Q10) exchange resins can be used to form the drug resin complex. Particularly suitable resins for use in the present invention are those which allow the rapid release of Co-Q10 in the gastrointestinal tract. Illustrative examples employ Amberlite IR-120, a cationic exchange resin that contains 20-30 mesh (590-840 um) spherical particles as a model large particle resin and Amberlite XE-69, which is 100-200 mesh fractured resin particles of Amberlite IR-120, as a model small particle resin. The parent resin of IR-120 and XE-69 is described by the manufacturer as a gel-type divinylbenzene sulfonic acid cation exchange resin that swells in water, regardless of pH levels. Other suitable ion exchange resin candidates include synthetic ion exchange resins with different polymeric matrices (e.g., methacrylic, acrylic, phenol formaldehyde), ion exchange agents with cellulosic or dextran polymer matrices, and inorganic ion exchange matrices. The resins preferably do not have inherent toxic properties.

Adsorption or adhesion of the drug onto the ion exchange resin particles to form the drug resin complex is a well-known technique. Briefly, the drug is mixed with an aqueous suspension of the resin and the complex is then dried. Adsorption or adhesion of drug onto the resin is detected by a change in the pH of the reaction medium. Resin particle size can range from nanosized up to about 1000 μm, depending in part on the format of the Co-Q10 being implemented.

Compositions of the invention also avoid the inclusion of a glyceryl ester having one or more $C_2$ to $C_7$ acyl group on its carbon backbone. In other words, compositions of the invention preferably do not contain a compound of the following structure,

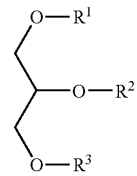

where each of R1, R2 and R3 independently is H or a $C_2$ to $C_7$ acyl group. In further embodiments, compositions of the invention also omit compounds having the foregoing chemical structure, where each of R1, R2 and R3 independently is H or a $C_8$, $C_9$ or $C_{10}$ acyl group.

In yet another, distinct embodiment of the invention, there are compositions that consist essentially of one or more of the following components: an effective amount of Co-Q10, rice bran oil, rice bran oil extract, a tocopherol, a non-ionic surface active agent such as polysorbate 80 or oleyl lactylic acid, and lecithin. As used herein, a compound that "consists essentially of" a list of specified components is a compound that excludes additional unspecified components (in particular, a glyceryl ester having the above chemical structure, where R1-R3 are independently hydrogen or a $C_2$ to $C_7$ acyl group) that would affect the basic and novel characteristics of the composition defined in the balance of a particular patent claim. As used herein, a "long-chain fatty acid molecule" is defined as a fatty acid-molecule having a hydrocarbon chain of at least eight carbons.

Methods of Making the Inventive Compositions

Co-Q10 formulations and compositions can be made by reference to the following representative methods.

In one embodiment, the various components initially are added to a suitable container at the concentrations specified herein. For example, rice bran oil, Polysorbate 80 and Olacta can be added to a container, followed by heating and mixing until a uniform or substantially uniform mixture is established. The skilled worker will appreciate that continued, slower mixing after uniformity is established can provide improved heat transfer.

After the temperature decreases to between about 160 degrees F and 78 degrees F, and more preferably between about 110 degrees F and 85 degrees F, and even more preferably between 100 degrees F and 90 degrees F, additional components can be added, including mixed tocopherols and the active ingredient, Co-Q10, which may be in charged or conventional form. This product then can be heated and mixed until the time when (i) the mixture appears uniform or substantially uniform in distribution and (ii) Co-Q10 is in solution. The temperature may be adjusted, as necessary, to urge the Co-Q10 into solution at the elevated temperature, which likely will be indicated by a transparent color in the mixture. Thereafter, the temperature can be decreased in a controlled manner, so as to prevent or minimize the amount of Co-Q10 that may elute out of the mixture.

A nano-particulate Co-Q10 formulation can, according to one aspect of the invention, be made in purified or substantially purified form. To this end, a sample of Co-Q10 can be made nanosized as described above, then be formulated into an aerosol composition, for example, as provided below.

Additionally, compositions can be made by suspending the nano particles in a suitable carrier base (similar to rice bran oil, tocopherols, etc.); filling nano particles into two-piece capsules; or creating an emulsion for topical or transdermal application.

Nanosized Co-Q10 also can be combined with various bioavailability-enhancing components of the invention to form a mixed composition. In this format, nanosized Co-Q10 is combined with a pre-cooled carrier(s) (i.e., preferably less than 90° C., more preferably less than 49° C., and most preferably less than 30° C. for a pre-cooled carrier). Then, a temperature of between about 5° C. and 40° C. is maintained, until at least a substantial amount of the Co-Q10 combines with the carrier(s).

Moreover, charged Co-Q10 can be combined with various bioavailability-enhancing components of the invention to form a mixed composition. In this format, the carrier may be neutral in charge or carry a net charge that is the opposite charge of the Co-Q10. Candidates for a charged carrier include the conventionally available resins used in pharmaceutical preparations, where the resins preferably carry a charge opposite the charge of Co-Q10.

Pharmaceutical Compositions

The invention provides various pharmaceutical formulations containing, at a minimum, (i) any Co-Q10 composition or formulation described above and (ii) a pharmaceutically acceptable carrier therefor. By "pharmaceutically acceptable" in this context is meant a carrier comprised of a material that is not biologically or otherwise undesirable. Pharmaceutical compositions for use in accordance with the present invention can be formulated in a conventional manner using one or more pharmacologically or physiologically acceptable carriers that contain excipients, as well as optional auxiliaries that facilitate processing of the active compounds into preparations which can be used pharmaceutically.

Proper formulation is dependent upon the route of administration chosen. For systemic injection, Co-Q10 can be formulated in aqueous solutions, preferably in physiologically compatible buffers. For transmucosal administration, penetrants appropriate to the barrier to be permeated are used in the formulation. Such penetrants are generally known in the art. For oral administration, Co-Q10 can be combined with carriers suitable for inclusion into tablets, pills, capsules, liquids, gels, syrups, slurries, and suspensions. For administration by inhalation, Co-Q10 is delivered in the form of an aerosol spray presentation from pressurized packs or a nebulizer, with the use of a suitable propellant. The source of Co-Q10 can be formulated for parenteral administration by injection, e.g., by bolus injection or continuous infusion. Such compositions can take such forms as suspensions, solutions or emulsions in oily or aqueous vehicles, and can contain formulatory agents such as suspending, stabilizing and/or dispersing agents. For application to the skin, Co-Q10 can be formulated into a suitable gel, magma, cream, ointment, or other carrier. For application to the eyes, the source of Co-Q10 can be formulated in aqueous solutions, preferably in physiologically compatible buffers.

The pharmaceutical composition of the present invention also includes combination products that comprise Co-Q10 and additional active ingredients. Such additional active ingredients include, but are not limited to, vitamins, minerals, amino acids, nutritional supplements, and therapeutic agents.

Softgels

For oral administration, it is preferred that a Co-Q10 composition of the invention is formulated into a soft elastic gelatin capsule unit dosage form, by using conventional methods well known in the art, such as in Ebert, Pharm. Tech, 1(5):44-50 (1977). Soft elastic gelatin capsules have a soft, globular gelatin shell, somewhat thicker than that of hard gelatin capsules. In such soft gel formats, gelatin is plasticized by the addition of plasticizing agent, e.g., glycerin, sorbitol, or a similar polyol. The hardness of the capsule shell may be changed by varying the type of gelatin used and the amounts of plasticizer and water. The soft gelatin shells may contain a preservative, such as methyl- and propylparabens and sorbic acid, to prevent the growth of fungi Co-Q10, the active ingredient, may be dissolved or suspended in a liquid vehicle or carrier, such as vegetable or mineral oils, glycols such as polyethylene glycol and propylene glycol, triglycerides, surfactants such as polysorbates, or a combination thereof.

Controlled-Release

In addition to the common dosage forms set out above, the compounds of the present invention may also be administered by controlled release mechanism, delivery devices, or both, as are well known to those of ordinary skill in the art, such as those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, the disclosures of which are hereby incorporated by reference. These pharmaceutical compositions can be used to provide slow or controlled-release of Co-Q10 using, for example, hydropropylmethyl cellulose in varying proportions to provide the desired release profile, other polymer matrices, gels, permeable membranes, osmotic systems, multi-layer coatings, microparticles, liposomes, microspheres, or the like, or a combination thereof.

The controlled-release of Co-Q10 may be stimulated by various inducers, for example pH, temperature, enzymes, water, or other physiological conditions or compounds. The term "controlled-release component" in the context of the present invention is defined herein as a compound or compounds, including polymers, polymer matrices, gels, permeable membranes, liposomes, microspheres, or the like, or a combination thereof, that facilitates the controlled-release of Co-Q10 in the pharmaceutical composition.

Advantages of controlled-release formulations may include: 1) extended activity of the drug; 2) reduced dosage frequency; and 3) increased patient compliance. Controlled-release formulations of the invention are designed to initially release an amount of drug that promptly produces the desired therapeutic effect, followed by the gradual and continual release of other amounts of drug to maintain this level of therapeutic effect over an extended period of time. In order to maintain this constant level of drug in the body, Co-Q10 is released from the dosage form at a rate that will replace the amount of Co-Q10 being metabolized and excreted from the body.

Aerosols

The present invention also provides a method for delivering an effective amount of a pure or substantially pure composition of nanosized Co-Q10 in the form of an aerosol, particularly through the membranes of the mouth or lungs. In this context, the concentration of the coenzyme-Q10 delivered is an amount sufficient to be effective in treating or preventing a disorder or to regulate a physiological condition in an animal or human. The specific concentration or amount of nanosized Co-Q10 administered will depend on the parameters determined for the agent and the method of administration, e.g. nasal, buccal and pulmonary. For example, nasal formulations tend to require much lower concentrations of some ingredients in order to avoid irritation or burning of the nasal passages. To provide a suitable nasal formulation, an oral formulation may be diluted to up to 10-100 times.

A mixed aerosol formulation of Co-Q10 may be prepared by mixing an aqueous solution of nanosized Co-Q10, an alkali metal C8 to C22 alkyl sulphate, conventionally available aerosol forming compounds, and optionally the phenolic compound. Aerosol forming compounds may be added at the same time or after addition of the alkali metal alkyl sulphate. Mixed aerosol will form with substantially any kind of mixing of the ingredients. Vigorous mixing is preferred, however, in order to provide and maintain smaller sized particles.

In one particular method, a first aerosol composition that contains the pharmaceutically active Co-Q10 and at least the alkali metal alkyl sulphate is prepared. This first aerosol composition then is mixed with at least three aerosol forming compounds, for example, to form a mixed aerosol composition. In another method, the aerosol composition is prepared by vigorously mixing: pharmaceutically Co-Q10 in nano-form, alkali metal alkyl sulphate and at least one of the aerosol forming compounds, followed by the addition of at least two further aerosol forming compounds.

Phenol and/or m-cresol may be added to the mixed aerosol composition to stabilize the formulation and protect against bacterial growth. Or, the phenol and/or m-cresol may be added with the micelle-forming ingredients. An isotonic agent, such as glycerin, also may be added after formation of the mixed micellar composition. The formulation then can be administered into an aerosol dispenser, which then is charged with a propellant (e.g., hydrogen-containing chlorofluorocarbons, hydrogen-containing fluorocarbons such as dimethylfluoropropane and tetrafluoropropane, dimethyl ether, diethyl ether, tetrafluoroethanes such as HFA 134a (1,1,1,2 tetrafluoroethane), butane and isobutene).

The propellant, which is under pressure, exists in liquid form in the dispenser. In the present invention, when the composition of the present invention is in a dispenser, the aqueous phase is separated from the propellant phase, requiring shaking of the dispenser prior to dispensing a portion of the contents, e.g., via a metered valve. A dispensed dose of Co-Q10 is propelled from the metered valve in the form of a fine spray.

When administered as an aerosol, Co-Q10 particles are less than about 1000 nm, preferably about 500 nm or less, more preferably about 300 nm or less, and most preferably less than about 100 nm. Mixed aerosol tend to be smaller than the pores of the membranes in the oral cavity or the gastrointestinal tract, which helps the encapsulated molecules penetrate efficiently through the mucosal membranes of the oral cavity.

The desired size of aerosol droplets sprayed from the aerosol dispenser can depend upon the route of administration. For example, for deposition in the lungs, particle sizes of less than about 5 µm are preferred whereas for absorption in the buccal cavity of the mouth, particle sizes of about 6-10 µm are preferred. Administration of Co-Q10 into the buccal cavity can occur by spraying the Co-Q10 into the mouth, without inhalation, so that the droplets stay in the mouth rather than be drawn into the lungs.

Two-Piece Capsule

An effective amount of Co-Q10 also can be administered to a patient in the form of a two-piece capsule. A suitable two-piece capsule can handle a liquid without leaking, provided that it is properly sealed or that the liquid is converted into a solution which is either solid or semi-solid at room temperature. If the solid or semi-solid solution contained within the two-piece capsule is a concentrated or highly concentrated solution of Co-Q10, then the advantages possessed by a solution over a suspension are made available to both the user and the manufacturer, namely, the advantage of a faster and more uniform absorption of Co-Q10 is available to the user of the two-piece capsule, while the advantage of uniformity of the batch is available to the capsule manufacturer.

Non-Animal Film System

The present invention also contemplates the use of a non-animal film system for affective administration of Co-Q10. A non-animal film system has a broad range of applications including dietary supplements, confectioneries, nutritionals, prescription and OTC pharmaceuticals. Such systems, e.g., capsules, are animal-free, non-toxic, non-allergenic, biodegradable and comprised of GRAS (Generally Regarded As Safe) ingredients that are commonly used in food and pharmaceutical applications. A non-animal film system can contain liquids, suspensions, pastes or dry powders and can effectively deliver a second active agent in addition to Co-Q10.

Topical Application/Transdermal Application

Compositions suitable for topical use on the skin can be in the form of an ointment, cream, lotion, paste, oil or spray. Carriers suitable for such use include petrolatum, lanolin, polyethylene glycols, alcohols and combinations of these substances. Typically, the "active ingredient" in such products is in a concentration of from about 0.1 to about 15% by weight of the composition, for example from about 0.5 to about 2%. The methods for preparing such topically applied compositions are well known in the art.

Compositions suitable for transdermal administrations can be in the form of single plasters which are suitable for long term close contact with the skin. Such plasters would contain the active ingredient in an aqueous solution which is buffered where appropriate, dissolved and/or dispersed in an adhesive or dispersed in a polymer. A suitable active ingredient concentration is about 1% to 35%, preferably about 3% to 15%. The methods for making transdermal patches are well known in the art.

Injectable Application

Methods for making compositions suitable for parenteral administration are well known in the art and are applicable to the present invention. Such methods generally involve mixing the active ingredient in a sterile aqueous solution, which is preferably isotonic with the blood of the recipient. Injectable compositions generally contain from about 0.1% to about 7.5% of the active compound.

Methods of Administering Inventive Co-Q10 Formulations/Compositions

Co-Q10 formulations/compositions of the invention and pharmaceutical formats thereof can be used to treat any number of conditions. "Treat" as used herein refer to reduction in severity and/or frequency of symptoms, elimination of symptoms and/or underlying cause, prevention of the occurrence of symptoms and/or their underlying cause, and improvement or remediation of damage that is associated with a particular condition.

The compositions according to the invention can be administered in a circumstance in which increased Co-Q10 levels are desired. Disease states, disorders or conditions which may be treated include but are not limited to age-related degenerative diseases, periodontal disease, certain blood circulation diseases, impaired memory, fatigue, coronary disease, irregular heartbeat, high blood pressure, immune system impairment, and the aging process. The amount of Co-Q10 to be administered depends upon the degree of the effect desired. Those skilled in the art will derive appropriate dosages and schedules of administration to suit the specific circumstances and needs of the patient. Typically, dosages are from about 0.1 to about 100, preferably from about 0.5 to about 50, most preferably from about 1 to about 20, mg/kg of body weight.

If a formulation of modified pure Co-Q10, e.g. nanosized Co-Q10, is administered to a patient (e.g., as an aerosol), then any safe amount of Co-Q10 can be used, but preferably ranges from 0.1 to 5,000 mg per dose or dosage unit.

The invention claimed is:

1. A composition comprising coenzyme-Q10 having a net positive or net negative ionic charge.

2. A composition according to claim 1, wherein said coenzyme-Q10 is nanosized crystalline coenzyme-Q10.

3. A composition according to claim 2, wherein said nanosized crystalline coenzyme-Q10 has an average effective particle size of less than about 1000 nanometers.

4. A composition according to claim 2, wherein said nanosized crystalline coenzyme-Q10 has an average effective particle size of less than about 300 nanometers.

5. A composition according to claim 1, further comprising a suitable carrier or excipient therefore.

6. A composition according to claim 1, further comprising at least one lipid-based or lipid-soluble compound.

7. A composition according to claim 6, wherein said lipid-based or lipid-soluble compound is selected from the group consisting of a tocopherol, a vegetable oil and lecithin.

8. A composition according to claim 7, wherein said tocopherol is selected from the group consisting of an alpha tocopherol, a beta tocopherol and a gamma tocopherol.

9. A composition according to claim 7, wherein said vegetable oil is selected from the group consisting of palm, coconut, palm kernel, palm stearin, coffee, soya, soybean oil, safflower, canola, rapeseed, flax, cotton, cottonseed, wheat germ oil, maize germ oil, sunflower, lucerne oil, poppy oil, red kuri oil, sesame oil, rapeseed oil, evening primrose oil, millet oil, barley oil, quinoa oil, rye oil, candlenut oil passionflower oil, and rape seed oil.

10. A composition according to claim 1, further comprising at least one hydro-dispersible or hydro-soluble compound.

11. A composition according to claim 10, wherein said hydro-dispersible or hydro-soluble compound is a non-ionic surface active agent.

12. A composition according to claim 11, wherein said non-ionic surface active agent is selected from the group consisting of lecithin, polysorbate 80 and oleyl lactylic acid.

13. A composition according to claim 1, further comprising a specifically charged resin.

14. A composition according to claim 13, wherein said coenzyme-Q10 is coated on said resin.

15. A composition comprising coenzyme-Q10 having a net positive or net negative ionic charge, wherein said coenzyme-Q10 is nanosized crystalline coenzyme-Q10.

16. A composition according to claim 15, further comprising at least one lipid-based or lipid-soluble compound.

17. A composition according to claim 15, further comprising at least one hydro-dispersible or hydro-soluble compound.

18. A composition according to claim 17, wherein said hydro-dispersible or hydro-soluble compound is a non-ionic surface active agent.

19. A composition according to claim 18, wherein said non-ionic surface active agent is selected from the group consisting of lecithin, polysorbate 80 and oleyl lactylic acid.

20. A composition comprising
coenzyme-Q10 having a net positive or net negative ionic charge, wherein said coenzyme-Q10 is nanosized crystalline coenzyme-Q10,
at least one lipid-based or lipid-soluble compound, and
at least one hydro-dispersible or hydro-soluble compound.

* * * * *